United States Patent
Haycock (10) Patent No.: US 10,568,323 B1
(45) Date of Patent: Feb. 25, 2020

(54) BEEHIVE MITICIDE DISPENSER

(71) Applicant: P J Staples Limited, Taupo (NZ)

(72) Inventor: Phillip John Haycock, Taupo (NZ)

(73) Assignee: P J Staples Limited, Taupo (NZ)

( * ) Notice: Subject to any disclaimer, the term of this patent is extended or adjusted under 35 U.S.C. 154(b) by 0 days.

(21) Appl. No.: 16/546,251

(22) Filed: Aug. 20, 2019

(30) Foreign Application Priority Data

Aug. 29, 2018 (NZ) ........................................ 745836
Aug. 31, 2018 (NZ) ........................................ 745934

(51) Int. Cl.
*A01N 37/02* (2006.01)
*A01K 51/00* (2006.01)
*A01N 25/34* (2006.01)

(52) U.S. Cl.
CPC .............. *A01N 37/02* (2013.01); *A01K 51/00* (2013.01); *A01N 25/34* (2013.01)

(58) Field of Classification Search
CPC ......... A01N 37/02; A01N 25/34; A01K 51/00
See application file for complete search history.

(56) References Cited

FOREIGN PATENT DOCUMENTS

WO 2015/071890 A1 5/2015

OTHER PUBLICATIONS

Haycock, Phil, "Machine Working," Jul. 1, 2018, screenshots from video.
New Zealand International Property Office, First Examination Report, App. No., 745836, dated Dec. 21, 2018, pp. 1-6.
New Zealand International Property Office, Further Examination Report Postponed Acceptance, App. No., 745836, dated Jul. 31, 2019, p. 1.
Haycock, Phil, "Paper Tape Strips," May 6, 2018, available at https://www.youtube.com/watch?v=9ZzAR2DcowY&feature=youtu.be&t=103.
Sqeptick, "How to Make an Oxalic Acid-Glycerin Towel for Varroa Mite Treatment," Mar. 29, 2017, available at https://www.youtube.com/watch?v=rlgqElnjdXM.

*Primary Examiner* — Trevor Love
(74) *Attorney, Agent, or Firm* — Cahn & Samuels, LLP (57) ABSTRACT

A treatment device for a beehive includes a strip having at least one layer. The at least one layer is formed from a biodegradable material permeable to water, such as paper. At least one layer is saturated with a treatment fluid. A reinforcement or join is provided to or adjacent each longitudinal edge of the strip, to protect and/or reinforce the longitudinal edges to mechanically resist attack by bees in the hive.

18 Claims, 4 Drawing Sheets

BEEHIVE MITICIDE DISPENSER

I. TECHNICAL FIELD

The present invention relates to devices for dispensing a treatment solution within a beehive.

II. BACKGROUND ART

Beehives are made up of "boxes" each holding a number of frames on which bees build honeycomb which the beekeeper harvests. The boxes are stacked one on top of the other to form a stack. A standard box holds 8 or 10 frames.

Typically, the first and second box up from the ground contain the breeding areas of the hive (the brood), and the higher boxes are used to store the bees gathering honey.

The *Varroa* mite is a parasite which breeds within the brood in the breeding area of the hive, the bottom one or two boxes. The *Varroa* mite, also known as the *Varroa Destructor*, presents a serious threat to bee populations. The mite can damage bees directly, or indirectly by introducing bacterial and viral infections.

Known methods for treating the *Varroa* mite include hanging devices impregnated in an active substance (a miticide) within the hive. The active substance is toxic to the *Varroa* mite but non-toxic to the bees. The bees transfer the substance throughout the hive and to the mites through contact with the impregnated device, for example by crawling over the surfaces of the device.

One of the contributing factors in the current dire *Varroa* mite problem has been the expense of existing mitacide application devices. This expense of existing devices has forced many Beekeepers to under treat or fail to treat their hives which may have contributed to an explosion in mite numbers per season, aggravated by high hive densities.

The increase in mite numbers has facilitated the spread of mites from contaminated sites to clean sites, often to the despair of beekeepers who have spent a great deal of money keeping *Varroa* mites under control in their own operations. There are many anecdotal reports of existing synthetic miticides not working as designed. It is possible these reports are in fact the result of under treating due to the high expense of treatment devices.

Some hives have extremely well developed hygienic traits which causes the bees to vigorously work at removing any foreign object from the hive, by 'chewing' through a foreign object with their mandibles. This trait presents a major challenge when designing a device that will be placed in a hive.

Due to the bees' trait of working to remove foreign objects, devices for providing a miticide to a hive are typically made from a plastics/polymer material, e.g. impregnated polymer strips, since the bees are incapable of removing/destroying the plastic devices. However, the plastic devices are extremely environmentally unfriendly. Bee keepers can accumulate large volumes of the used plastic devices, and this plastic waste can be difficult to legally dispose of due to its inherently toxic nature.

III. SUMMARY OF THE INVENTION

Figure 1A:
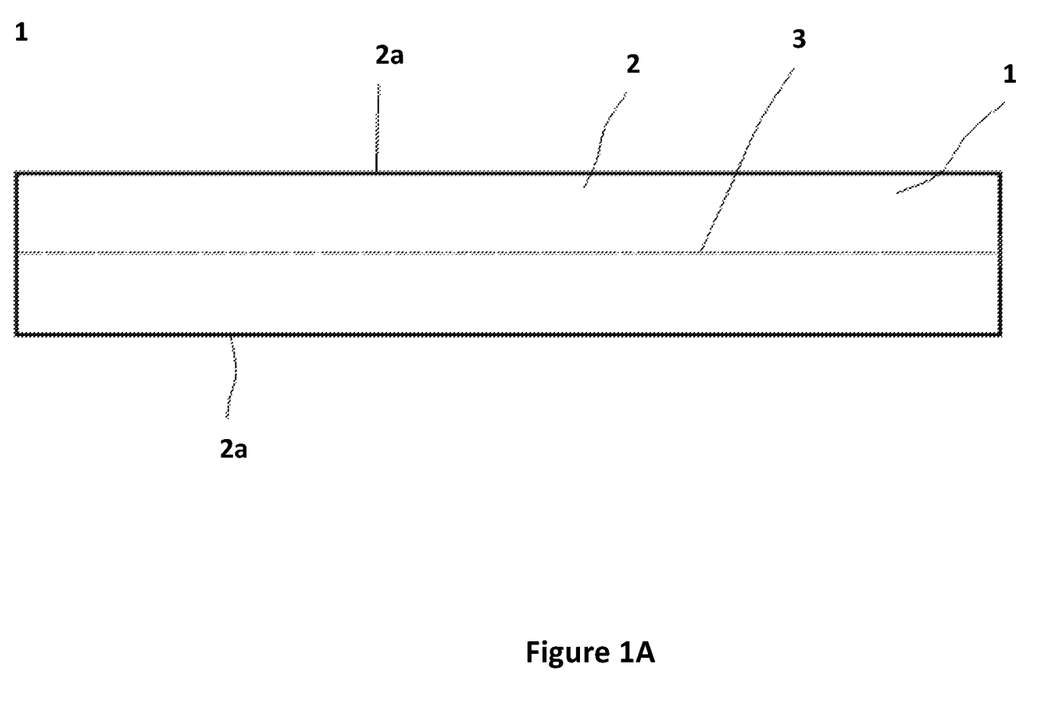
FIGS. 1A and 1B show a side view and end view of a prior art miticide dispensing device comprising three layers of paper tape joined together by a single row of stitching.
Figure 1B:
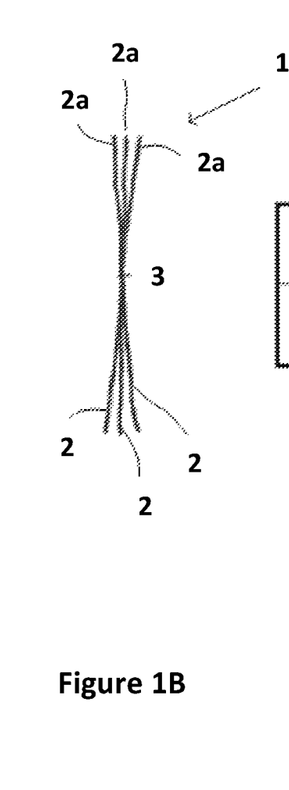

To address this environmental issue, the inventor developed a miticide dispensing device illustrated in FIGS. 1A and 1B. The device 1 comprises three layers of paper 2 soaked in a miticide. Each layer 2 is a Kraft paper tape, typically used as drywall joint tape, for example Gib® jointing tape. The three layers are held together by a single row of stitching 3 located along a longitudinal center of the tape. The layered device is soaked in a miticide and soaks up approximately twice its own weight. The miticide consists of a solution of 35% oxalic acid in glycerine. The device is bent into a 'staple' shape to be hung over a frame in the hive.

The device administers the miticide slowly over an extended period of time. During the course of performing their individual and collective hive duties, the bees walk over the wetted surface area of the outer surfaces of the outer layers, and contact the miticide, and then spread the miticide throughout the hive. The miticide inevitably contacts the *Varroa Destructor*, killing it.

As the bees transfer the miticide solution away from the surface of the outer layers, solution carried by the bees from the outer layer is replaced by solution stored within the layered structure of the device. The solution soaks from the inner layer to the outer layers through contact between the layers at the line of stitching. The miticide solution cannot jump an air gap between the layers of the device. This results in an extended period for the release or availability of the active ingredient from the outside surface of the device.

Since the mites breed within the brood area, the devices are placed in the brood area of the hive and not usually in the honey storage area. As described above, the brood area in some hives is just the bottom box and in others it is the lower 2 boxes.

Choosing how many treatment devices to place in a hive is a management decision of the Beekeeper. If the Brood is restricted to a single lower box then that box will require 4 staples typically placed astride frames 2,4,6 and 8. If the hive has a 2-box brood then the lower box is treated as described and the second from bottom box gets just 3 staples, placed astride frames 3,5 and 7.

The treatment device will have varying life spans depending on where in the hive a device is placed. The devices last longer the further they are from the geometric center of the brood nest. This is because the bees are especially fussy about keeping the brood nest free of foreign objects. However, the center of the brood nest is precisely where the treatment is most needed.

Some of the bees of the hive will be recruited to attack and remove the staple and it is the physical properties of the staple that determine its ability to resist this attack. The bees can remove the paper layers 2 with their mandibles during the brood cycle. The paper tape is resilient and resistant to the bees determined efforts to remove it, however where the bees are persistent and determined they eventually win out, requiring replacement of the staples.

It is a critical requirement that the miticide dispensing device can resist the bees' removal attempts long enough to span at least one 28-day breeding cycle. This is because the *Varroa* mite breeds within the bees' brood and while sealed in this brood the mite is protected from any miticide within the hive. The growing mites will not be exposed to the active ingredient of the device until they emerge from the brood with the young bees. Although the device must remain effective for at least 28 days, the bee industry demands a miticide treatment to last significantly longer than one brood cycle, and 56 days is an accepted minimum treatment duration.

It would be a significant advantage to the beekeeping industry to provide a miticide dispensing device that is cost effective, so that beekeepers are not tempted to undertreat or avoid treating their hives.

It would be a further significant advantage to the beekeeping industry to provide a miticide dispensing device that is substantially biodegradable and which has an improved resistance to the bees' attempts to remove the device from the hive.

All references, including any patents or patent applications cited in this specification are hereby incorporated by reference. No admission is made that any reference constitutes prior art or forms part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

It is an object of the present invention to address one or more of the foregoing problems or at least to provide the public with a useful choice.

According to a first aspect of the present invention there is provided a treatment device for a beehive. The treatment device comprises a longitudinal strip comprising at least one layer. The or each layer is formed from a biodegradable material permeable to water, and at least one layer and preferably all layers are saturated with a treatment fluid. A reinforcement or join is provided to or adjacent each longitudinal edge of the strip, to protect and/or reinforce the longitudinal edges to mechanically resist attack by bees in the hive. The reinforcement or join presents a longitudinal barrier or shield at or adjacent each longitudinal edge to mechanically resist bees in the hive attacking and removing the layer(s) of the strip.

In some embodiments, the device comprises a plurality of layers, with at least one said layer saturated with the treatment fluid. The layers are joined together to allow for the transfer of the treatment fluid between layers as the treatment fluid is removed from an outer surface of the device.

In some embodiments, the device comprises at least three layers, the layers joined together to allow for the transfer of the treatment fluid from an inner layer to an outer layer as the treatment fluid is removed from an outer surface of the device.

In some embodiments, the longitudinal strip comprises more than three layers. In some embodiments, the longitudinal strip comprises four layers, two inner layers sandwiched between two outer layers.

In some embodiments, the layers are joined together by at least two longitudinal joins spaced apart across the width of the strip.

In some embodiments the device comprises two or three longitudinal joins. In at least one embodiment, the device comprises a join at or adjacent each longitudinal edge. The joins at or adjacent the longitudinal edges join and/or hold the layers together at the longitudinal edges to thereby reinforce the longitudinal edges of the device to mechanically resist attack by bees in the hive. In a further embodiment, the device comprises a join nearer to each longitudinal edge of the strip than the longitudinal center of the strip. For example, the device comprises a join within 10 mm of each longitudinal edge, or within 8 mm of each longitudinal edge. The layers are held together in direct contact at and/or adjacent to each longitudinal join.

In some embodiments, the reinforcement or join shields the longitudinal edge to mechanically resist attack by bees in the hive.

In at least one embodiment, each join or reinforcement is a line of stitching. In a preferred form, the stitching is made from a biodegradable thread.

In at least one embodiment, the stitching comprises a maximum stitch length of 5 mm.

In some embodiments, each reinforcement or join at a longitudinal edge of the strip comprises an overlock stitch pattern. Alternatively, in some embodiments, the reinforcement is a metallic material provided to the longitudinal edge of the strip, and/or an edge region of the strip is rolled or folded over on itself to present a double or triple or higher multiple strip thickness at the longitudinal edges.

Providing reinforced edges and/or joins at or adjacent the edges presents a structure that the bees find difficult to remove, as the bees cannot work through the reinforced edge and/or more than one layer at a time.

Increasing the number of layers increases the holding capacity of the device, lengthening the dispensing life of the device. This is particularly useful when using multiple joins, as increasing the joins causes an increased transfer rate from the inner layer or layers to the outer layers.

In a most preferred form of the invention the treatment fluid is a miticide, in particular for treating (killing) the *Varroa Destructor*.

In some embodiments, the treatment fluid is a solution comprising a carboxylic acid as an active ingredient. In at least one embodiment, the treatment fluid is a solution of carboxylic acid in food grade glycerine. In some embodiments, the carboxylic acid is oxalic acid.

In some embodiments, the solution comprises less than 35% carboxylic acid. In some embodiments, the solution comprises 25% to 35% carboxylic acid, or 25% to 30% carboxylic acid.

In a most preferred embodiment, the one or more layers is or comprises paper, and is preferably Kraft paper.

In some embodiments, the longitudinal strip is provided in a roll, to be cut into pieces prior to placement in a hive.

In many embodiments the reinforcement or join is a continuous reinforcement or join, providing little or no gaps along the barrier or shield in the longitudinal direction of the strip.

According to a second aspect of the present invention there is provided a treatment device for a beehive. The treatment device comprises a longitudinal multi-layered strip comprising at least three layers. Each layer is formed from a biodegradable material permeable to water, and at least one layer and preferably all layers are saturated with a treatment fluid. The layers are joined together by at least two longitudinal joins spaced apart across the width of the strip to allow for the transfer of the treatment fluid from an inner layer to an outer layer as the treatment fluid is removed from the outer layer. Each join presents a longitudinal barrier or shield at or adjacent each longitudinal edge to mechanically resist bees in the hive attacking and removing the layer(s) of the strip.

The second aspect of the invention may have one or more of the features described above in relation to the first aspect.

According to a third aspect, a method for treating a beehive by placing a treatment device according to the first or second aspects in a hive. The device is positioned within a beehive by folding the strip into a staple shape and hanging the strip over a frame within the hive to present the outer surfaces of the device for bees to walk over and disperse miticide throughout the hive.

According to a fourth aspect, a method for making a treatment device comprises: providing a strip comprising at least one layer, the or each layer formed from a biodegradable material permeable to water, providing a longitudinal reinforcement or join to or adjacent each longitudinal edge of the strip, to protect and/or reinforce the longitudinal edges to mechanically resist attack by bees in the hive, wherein the reinforcement or join provides a longitudinal barrier to mechanically resist bees in the hive attacking and removing the or each layer of the device, and soaking the strip in a treatment fluid to saturate the strip.

In some embodiments, the strip comprises a plurality of layers and the method comprises providing the plurality of layers and joining the layers together to allow for transfer of the treatment fluid between layers as the treatment fluid is removed from an outer surface of the strip during use.

In some embodiments, the method comprises providing the or each layer in a roll, unrolling the or each layer from the roll or rolls as a continuous strip, and providing the reinforcement or join to or adjacent each longitudinal edge of the continuous strip in a continuous process, cutting the continuous strip into individual strips, each individual strip to be placed in the beehive.

In some embodiments, the method comprises providing each layer in a roll, unrolling each layer and aligning and stacking the layers together to form a continuous strip, and providing the reinforcement or join to or adjacent each longitudinal edge of the continuous strip in a continuous process, and cutting the continuous strip into individual strips, each individual strip to be placed in the beehive.

In some embodiments, the method comprises rolling the continuous strip into a roll, unrolling the continuous strip from the roll and cutting into the individual strips.

In some embodiments, the strip or roll of continuous strip is stored dry and is soaked in the treatment fluid immediately prior to use.

The invention provides a device that is resilient to bees' determined efforts to remove the device from the hive, while also being formed from layers that a biodegradable, thus presenting a treatment device that has a useful life longer than a brood cycle and which can be easily disposed of by beekeepers. The device therefore presents a device that is sustainable and effective. The invention also provides a low-cost solution to the control of the *Varroa Destructor*, which improves the take up in use of the device by beekeepers, reducing the risk of beekeepers undertreating or not treating hives.

Unless the context suggests otherwise, the terms 'yarn' or 'thread' are used generally to describe any long slender flexible material capable of being used in stitching or sewing and may comprises one or many strands or filaments, i.e. multi or mono filament, and can include a metal filament or wire. These terms are not intended to suggest a particular makeup.

IV. BRIEF DESCRIPTION OF THE DRAWINGS

Further aspects of the present invention will become apparent from the ensuing description which is given by way of example only and with reference to the accompanying drawings.

In end views of the above figures gaps between layers may be exaggerated for clarity, to illustrate the structure of the devices.

V. DETAILED DESCRIPTION OF THE INVENTION

The inventor has devised an improved paper based miticide dispenser for beehives that has an extended life compared to the above described paper based miticide dispenser illustrated in FIGS. 1A and 1B.

Figure 2A:
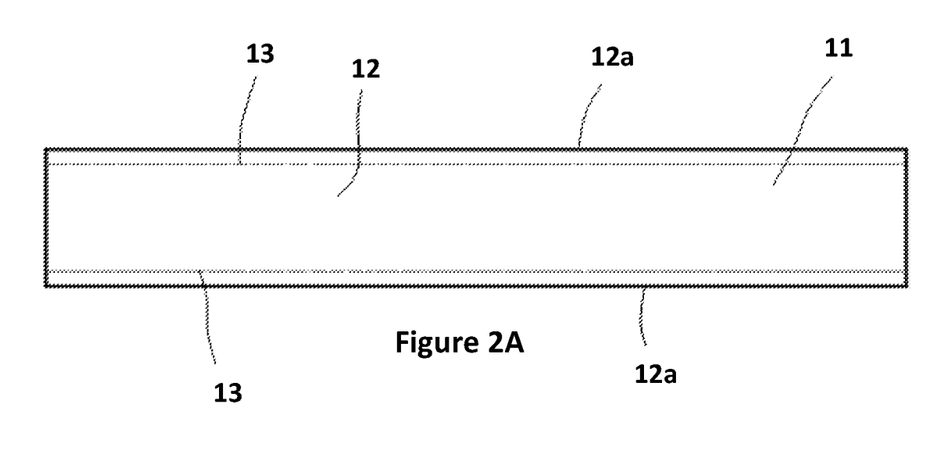
FIGS. 2A and 2B show a side view and end view of an improved miticide dispensing device comprising three layers of paper tape joined together by two rows of stitching, each row adjacent a longitudinal edge of the device.
Figure 2B:
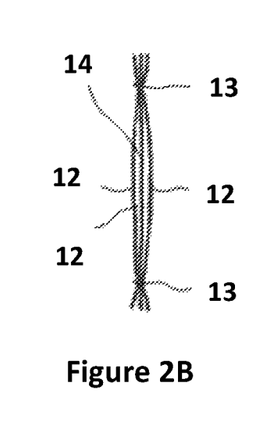

Initially with reference to FIGS. 2A and 2B, the improved device comprises a strip 11 comprising at least three layers of paper tape 12. At least one of the layers and most preferably all of the layers 12 are soaked in a miticide or other treatment fluid.

According to the present invention, the layers 12 are joined together by a plurality of longitudinal joins 13 spaced apart across the width of the tape. The joins 13 provide points of contact between the layers across the width of the strip. These contact points allow the miticide to transfer from the inner layer or layers to the outer layers as the bees remove the miticide from the outer surfaces of the outer layers.

In at least one embodiment, the multi-layered strip is soaked in miticide to saturate the layers with miticide prior to use. The strip is hung in a beehive so that bees can walk over surfaces of the strip. For example, the multi-layer strip is folded into a staple shape and hung over a frame within the hive, to present the outer surfaces of the device for the bees to walk over and disperse the miticide throughout the hive. The device may otherwise be hung in a hive for example from a piece of string or by a stick or rod placed through a hole in the strip with the stick or rod resting on adjacent frames within the hive.

The bees attack and remove material from the outer or longitudinal edges 12a of each individual layer of the multi-layered strip using their mandibles, to remove the device 11 from the hive. The bees remove the layers by working inwards from the edges of the layers towards the centre of the strip tearing pieces away from the edges, until the strip is mostly removed. Bees cannot remove layers other than via an edge of a layer.

By providing a plurality of joins between the layers, the improved device 11 presents a dense or closely packed layered structure that the bees find difficult to remove.

In at least one embodiment, a join is provided closer to each longitudinal edge than to the centerline of the strip. Preferably there is a join located adjacent each longitudinal edge. For example, the join is within about 10 mm, or 8 mm, or 6 mm or 5 mm or 4 mm of each longitudinal edge.

Placing a join line along each longitudinal edge of the multi-layered structure presents the bees with a structure that is dense and therefore more resilient than a device without this reinforcement.

The bees can remove material from the edge of an individual layer yet cannot remove material from more than one layer at a time, as multiple layers together present a thickness the bees cannot work through. Holding layers closely together at or near to an edge of the tapes results in a resilient device with an improved life extending well beyond the 28-day brood cycle.

In the embodiment of FIGS. 2A and 2B, the device 11 comprises two joins 13, each join near to a longitudinal edge 12a of the device. The embodiment of FIGS. 3A and 3B also includes a centerline join. The embodiment of FIGS. 4A and 4B have a join at each longitudinal edge 12a of the device.

In the illustrated embodiments each join 13 is provided as a row of stitches. Multiple layers 12 may be fed through a sewing machine, to stitch and hold the layers together. Each layer is preferably fed to the sewing machine from a roll and stitched together in a continuous process. Once the layers are stitched together, the multi layered device is rolled into a roll for further processing to be cut into individual lengths.

Each line of stitching additionally provides a continuous longitudinal barrier adjacent the strip edge that impedes the bees from working to remove strip material inwards from the join towards the centre of the strip. The bees may be able to remove layers from the longitudinal edge of the strip up to the barrier. As the bees remove material the edge of the strip moves further in towards the centre of the strip. However, the stitching presents a barrier to the bees, to impede or restrict the bees removing layers inwards of the barrier further towards a centre of the strip. This results in little to no material being removed inwards of and between the two joins adjacent the longitudinal edges of the strip.

Each device 11 is approximately 54 mm wide and around 200 mm to 600 mm long, with three or more layers. Hive boxes and the frames within the boxes vary in height, and the length of the device is determined by the height of the box and frames. A device length of 430 mm is suitable for a common sized box.

Figure 3A:
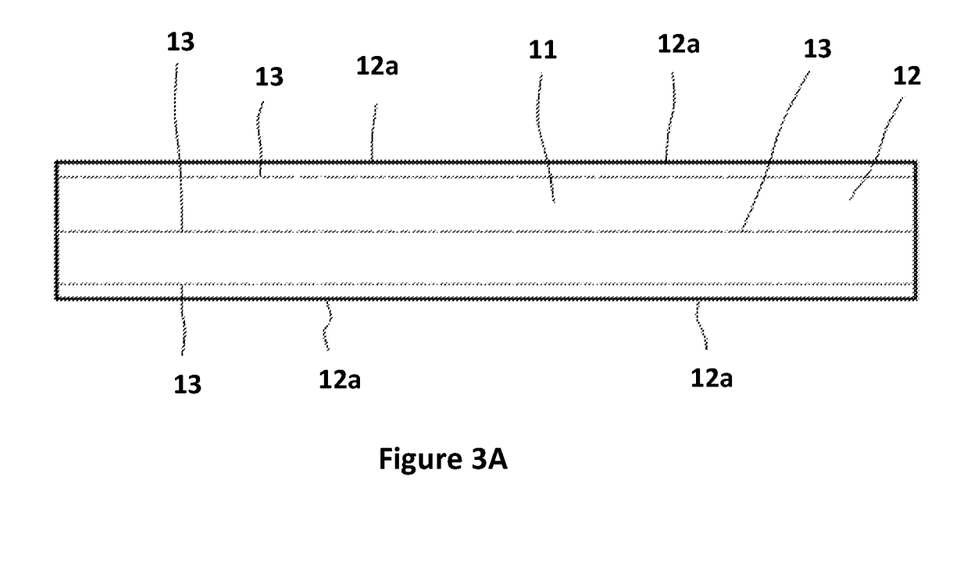
FIGS. 3A and 3B show a side view and end view of an improved miticide dispensing device comprising four layers of paper tape joined together by three rows of stitching, a central row and a row adjacent each a longitudinal edge of the device.
Figure 3B:
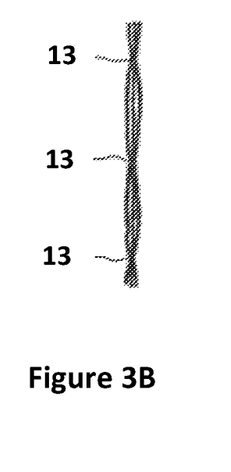
Figure 4A:
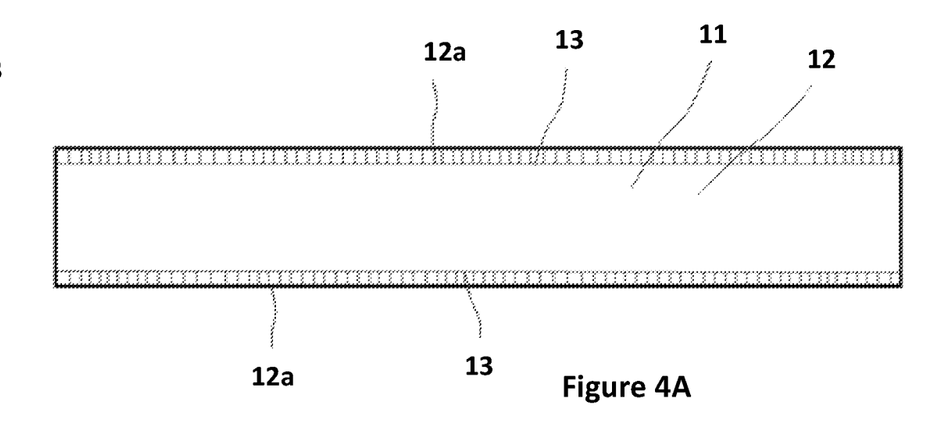
FIGS. 4A and 4B show a side view and end view of an improved miticide dispensing device comprising three layers of paper tape joined together by rows of stitching each row adjacent a longitudinal edge of the device and where the stitching is an overlocking stitch pattern.
Figure 4B:
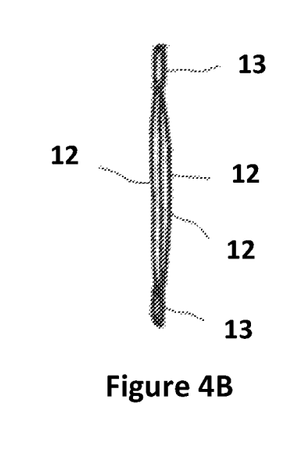

At the edges of the device 11 the row of stitching may be in the form of a straight stitch as shown in FIGS. 2A and 3A, or may be an over lock stitch, as shown in FIG. 4A to wrap over the edges of the tapes. Both forms of stitch present a barrier or shield to mechanically resist bees attacking and removing layers of the strip. The stitching presents loops of thread that the bees mandibles cannot extend about to 'chew' away the edge of the strip. The bees are able to remove the edge material up to the line of straight stitching however the stitching prevents or impedes the bees accessing an edge of the strip adjacent or at the stitching with their mandibles, preventing or impeding further removal of the strip beyond the stitching further towards the centre of the strip. The stitching presents a raised barrier or shield along the strip. The overlock stitch also reinforces/protects the edge by providing a cage or barrier or shield around the longitudinal edge, as discussed in more detail below. Such an arrangement may be more effective to prevent or resist attack by bees since the edge of the strip is protected from attack, rather than a line adjacent the strip edge.

The join preferably acts as a wick, to assist with transfer of miticide between layers 2. Where a thread or yarn is used to join layers together, the thread or yard can act as a wick by soaking up miticide and then via contact between the thread and the layers, allow transfer from one layer via the thread or yarn to an adjacent layer.

A suitable thread for stitching the layers together is a 40-weight polyester but could also be a biodegradable thread to form a treatment device which is 100% biodegradable. Although polyester is a plastic material and therefore non-biodegradable, a thread provides a significantly reduced amount of plastic waste compared to a treatment device that is formed completely from plastic.

In at least one embodiment, the stitching has a maximum stitch length of about 5 mm. A longer stitch length may be too loose to hold the layers together in a robust package.

Other joining methods may be employed other than or together with stitching. For example, layers may be bonded together with an adhesive. Each join may comprise a 'dashed' line of adhesive, such that areas between and/or around each 'dash' of adhesive within the join provide contact points between layers that allow for the transfer of miticide from one layer to the next. A glue line may be provided together with stitching, the glue line bonding layers and the stitching joining and also providing a wicking function. Bonding by adhesive alone may be less preferred as adhesive may not present a mechanical barrier to bees.

The layers are preferably formed from Kraft paper. The layers may be formed of paper tapes prepared for making joins between drywall linings, e.g. jointing tape sold under the Gib® brand. Drywall paper jointing tape is available as non-perforated and perforated. The non-perforated tape is a suitable layer material; however, the perforated tape material is particularly useful in the application of providing miticide since the small holes or perforations in the tape allow the material to quickly absorb solution even when tightly packed together within a container holding miticide. Spark perforated drywall joining tape is perforated with approximately 21,000 holes per square metre and each hole is approximately 0.15 mm diameter. The holes are so small that they do not present an edge on which the bees can work to remove the layer material. The paper has a relative density (with respect to water) of about 0.64. The paper has a thickness of about 0.2 mm.

As described above, by having a plurality of join lines, the layers are held closely together achieving a multi-layer construction that is harder for bees to remove with their mandibles. However, another outcome of having layers closely held together across the width of the device is that the contact area between layers is increased, resulting in a higher rate of transfer of miticide from an inner layer to an outer layer, compared to a device having a single join line. A higher transfer rate between layers can result in a dispensing device that dispenses more miticide from its outer surfaces than a device with a single join line.

A higher transfer rate from an inner layer to an outer layer can result in a higher dosing rate from the outer surfaces of the device over a shorter period of time, compared to a device with a single join line. To ensure the device does not dispense and therefore run out of miticide too quickly, an additional inner layer may be provided, so that the holding capacity of the device is increased. For example, one additional layer may be provided, such that the device has four layers, i.e. two inner layers sandwiched between two outer layers. More than four layers may be provided.

A further modification is to use a miticide with a lower concentration of active ingredient, to account for higher rate of transfer from an inner layer to an outer layer provided by multiple joins across the width of the device.

For example, a three-layer device that is 54 mm wide and 430 mm long has a dry weight of around 10 grams and will soak up about 20 grams of miticide solution. For a solution containing 35% oxalic acid and 65% glycerine, a single device contains 7 grams of oxalic acid (the active ingredient). Providing four devices in a single box gives 28 grams of active ingredient per box. This system provides a steady supply of oxalic acid in glycerine for up to 4-months depending on where the device is situated in the hive, the strength (population) of the hive and the genetic make-up of the bees in the hive.

Increasing the number of layers from three layers to four layers increases the holding capacity from 20 grams of miticide to 26.7 grams of miticide per device and a total of about 107 grams for a box containing four devices. To provide the same dosing level of 28 grams of active ingredient per box requires a solution of about 26% oxalic acid and 74% glycerine.

While oxalic acid in glycerine is provided as an example miticide, other solutions may be provided to treat a hive. For example, another carboxylic acid other than oxalic acid may be provided, such as acetic acid. Changing the type of acid or active ingredient periodically may reduce a risk of the *Varroa* mite developing an immunity to the active ingredient being used.

Another example treatment fluid is Thymol dissolved in isopropyl alcohol which is then carried in oil (for example vegetable oil) to also treat for *Varroa* mites.

The device 11 may be suitable for dispensing other substances to a hive, other than a miticide. The device is suitable for dispensing any liquid of a viscosity that can flow from a saturated inner layer to a less saturated outer layer. The device may be used to provide substances to treat pests other than the *Varroa Destructor*. For example, oxalic acid is also effective in the control of the wax moth. Other treatment fluids may be provided to control other pests such as the small hive beetle.

The device comprising a plurality of spaced apart join lines also provides a 'pocket' structure comprising an opening at each end between an inner layer and each outer layer. This structure provides a means by which beekeepers or researchers can add extra or alternative ingredients that may not be easily mixed in a solution to be soaked in the material of the layers. Solid form ingredients may be held in a pocket 14 (see FIG. 2B) formed between two join lines and two layers.

Other material types other than paper may also be used for the layers. The sheet material of the layers must be permeable to liquid, and as a reference permeable to water or a liquid of similar viscosity. However, to achieve the main benefit of the present invention of an environmentally friendly product, the sheet material forming the layers should be biodegradable.

Figure 6:
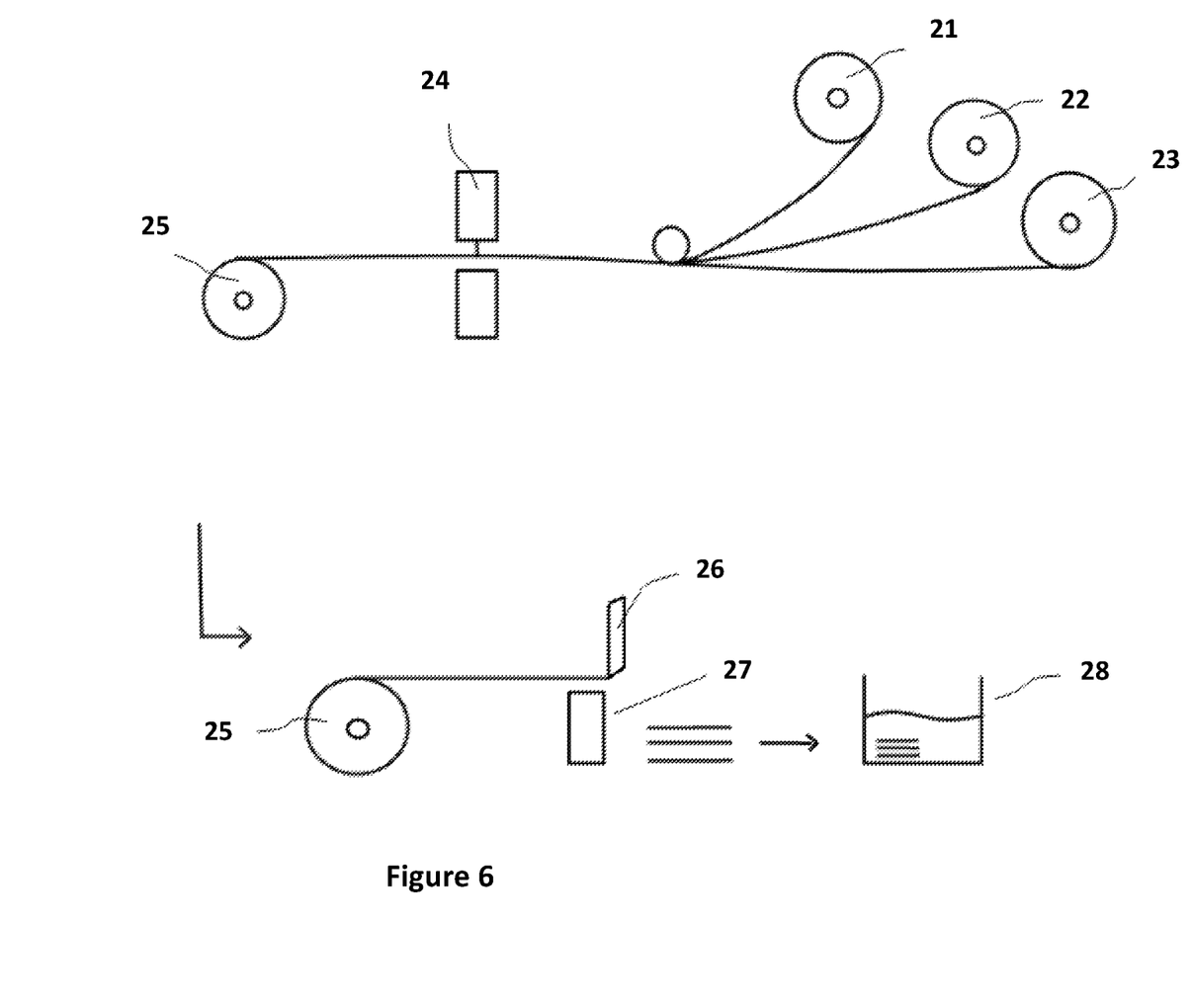
FIG. 6 is a schematic representation of a method for making a device for treating a beehive.

A method of making the device is partly described above. With reference to FIG. 6, a preferred method includes providing each layer 12 in a roll 21, 22, 23 and feeding each layer 12 from the roll to create a stack and joining the layers together in the stack to create a continuous strip comprising a plurality of layers. In a preferred embodiment the layers are stitched together by a sewing/stitching machine 24. The strip comprising a plurality of layers may be immediately cut into individual pieces or strips, or the strip comprising a plurality of layers may be coiled into a roll 25 to be provided as an input material to a subsequent cutting process 26.

The roll of multi-layered tape 25 may be soaked in a miticide, or the individual strips 27 once cut from the roll of multilayered tape may be soaked in a miticide. For example, a roll of multi-layered tape may be provided to a beekeeper dry or presoaked with miticide. The beekeeper can then cut pieces off the roll as required when treating a hive. This supply method is less preferred as a beekeeper may under treat a hive by cutting strips too short, resulting in a less than ideal amount of miticide in a hive.

Once the strip of a plurality of layers is cut into individual pieces or strips, for example using a guillotine 26, the strips are stacked together in a container, such as a 20 litre pail 28. For example, for a three-layer strip, a 20 litre pail can hold around 400 strips. The strips may be stored dry until the treatment devices are required. The dry strips and miticide may be sent to a beekeeper in separate containers. The beekeeper can then add the miticide to the container holding the strips according to instructions. A container holding 400 strips each with a 10 gram dry weight requires an 8-kilogram solution of miticide to completely saturate all 400 strips in the container, however a larger amount of solution is preferably provided to ensure saturation of all strips, for example a 10-kilogram amount of solution provided to soak 400 10-gram strips. The strips become fully saturated after being soaked in miticide in a few seconds to hours or days depending on the size of the bundle of strips being soaked and how tightly they are packed in a container. 400 strips 54 mm×430 mm packed in a pail can take a few hours to soak. Soaking may be done immediately before use, for example, soaking in miticide over night for use the next day is a convenient approach. Once soaked, the devices are ready to be bent into a staple shape and placed in the beehives over frames of the hive.

Alternative Embodiments

The above described embodiments, comprise a longitudinal strip of at least three layers.

Figure 5A:
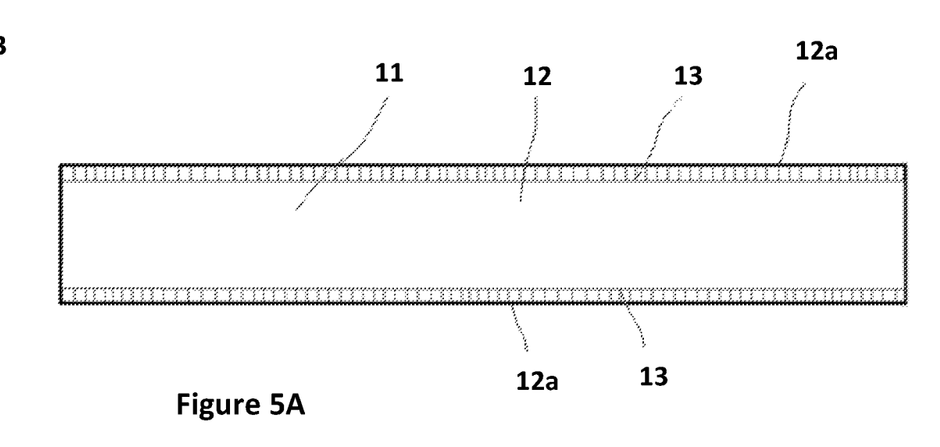
FIGS. 5A and 5B show a side view and an end view of an improved miticide dispensing device comprising a single layer of paper tape with reinforced edges.
Figure 5B:
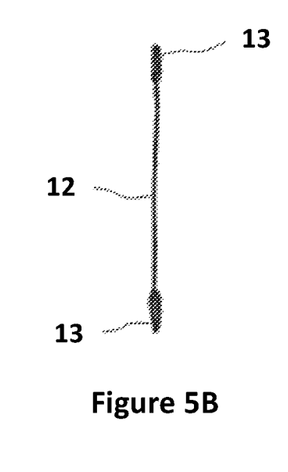

In alternative embodiments, a treatment device may comprise a single layer strip or a strip comprising two layers, with edges of the single or double layer strip reinforced to prevent or resist bees removing material from the edges of the strip. For example, reinforcing or a barrier may be provided at or adjacent the edges of a double or single layer strip by an overlocking stitch or a straight stitch adjacent the edge of the single or double layer strip. An overlocking stitch provides an additional benefit of looping around the longitudinal edge of the strip such that little material is removed, even from the original longitudinal edge of the strip. FIGS. 5A and 5B shows a single layer material with reinforced edges provided by an overlock stitch pattern. The overlock stitch pattern reinforces the edge by providing a barrier or 'cage' or shield around the edge which prevents or restricts the bees accessing the edge of the strip with their mandibles, much like a shielding protection device applied to a padlock to protect the padlock from being cut by a bolt cutter. In some embodiments, a steel wire may be used as the 'thread' to reinforce the edge by shielding the edge from the bees' mandibles. The bees are incapable of cutting through the steel wire. A low carbon steel wire will degrade by rusting and will degrade together with the biodegradable layer 12. A device 11 comprising a degradable edge reinforcement or join together with a biodegradable layer presents a low to zero impact on the environment.

Other reinforcing or barrier methods are possible. For example, a metallic material such as a metal foil may be provided to the edges, for example by crimping or bonding the foil to the edges. The metal foil may be provided to the edges to join multiple layers together at the edges of the strip, for example by crimping.

A further structure to reinforce edges is to roll or fold an edge portion of the material over on itself to create a double or triple or higher multiple strip thickness at the edges.

Where a folded edge is provided to a multi-layer strip, the folded edge also forms a join between the layers.

The bees are incapable of removing a layer material other than from an exposed edge of the material. Thus, by providing reinforcing or a barrier to the edges of the layer or layers, i.e. by strengthening or shielding, the device becomes resilient to the bees' efforts to remove the device from the hive. In embodiments comprising two or more layers, a longitudinal join at or adjacent the edge provides a reinforcing to the edge by joining or holding the layers together at the edges. As described above, the multi-layer edge provides a thickness that the bees struggle to remove.

Where a single or double layer strip is provided, more strips or longer strips are preferably provided to the hive. Referring to the treatment solution example above of 80 grams of 35% Oxalic acid to a hive box, a single layer 5 4 mm×430 mm×0.2 mm strip holds around 6.7 grams of solution, thus the box will require 12 strips. Alternatively, a heavier thickness layer material could be used to provide an increased holding capacity.

Higher loadings of active ingredient can also be used, for example 50% oxalic acid in glycerine.

A treatment device according to the present invention provides one or more of the following benefits:

The treatment device reduces plastic waste since at least the one or more layers of the device is/are biodegradable.

The treatment device provides a low-cost solution for the treatment of the *Varroa Destructor*, avoiding a temptation of some beekeepers to undertreat or not treat at all.

The treatment device, while comprising biodegradable material, is resistant to bees' determined efforts to remove it from the hive.

The treatment device is capable of providing treatment throughout a full brood cycle and with treatment times extending up to 4-months due to its mechanical resiliency.

An embodiment comprising biodegradable joins or reinforced edges, i.e. joins or reinforcement provided by a thread of natural fibres such as cotton, is 100% biodegradable.

The invention may also be said broadly to consist in the parts, elements and features referred to or indicated in the specification of the application, individually or collectively, in any or all combinations of two or more of said parts, elements or features.

Aspects of the present invention have been described by way of example only and it should be appreciated that modifications and additions may be made thereto without departing from the scope thereof as defined in the appended claims.

What I claim is:

1. A treatment device for a beehive comprising:
a strip comprising at least one layer, the or each layer formed from a biodegradable material permeable to water which is capable of being removed by bees,
the at least one layer is saturated with a miticide, and
a longitudinal reinforcement or join provided to or adjacent each longitudinal edge of the strip, the reinforcement or join presenting a longitudinal barrier or shield at or adjacent each longitudinal edge to mechanically resist bees in the hive attacking and removing the layer(s) of the strip,
wherein each join or reinforcement is a line of stitching.

2. The treatment device as claimed in claim 1, wherein the device comprises a plurality of layers, at least one said layer saturated with the miticide, and wherein the plurality of layers are joined together to allow for the transfer of the miticide between layers as the miticide is removed from an outer surface of the device.

3. The treatment device as claimed in claim 2, wherein the treatment device comprises at least three layers, the layers joined together to allow for the transfer of the miticide from an inner layer to an outer layer as the miticide is removed from an outer surface of the device.

4. The treatment device as claimed in claim 2, wherein the layers are joined together by at least two longitudinal joins spaced apart across the width of the strip.

5. The device as claimed in claim 1, wherein the reinforcement or join shields the longitudinal edge to mechanically resist attack by bees in the hive.

6. The device as claimed in claim 1, wherein the stitching is made from a biodegradable thread.

7. The device as claimed in claim 1, wherein each line of stitching at a longitudinal edge of the strip comprises an overlock stitch pattern.

8. The device as claimed in claim 1, wherein the miticide is a solution of carboxylic acid in food grade glycerine.

9. The device as claimed in claim 1, wherein one or more layers is or comprises paper.

10. The device as claimed in claim 9, wherein the paper is Kraft paper.

11. The device as claimed in claim 1, wherein the strip is provided in a roll, to be cut into pieces prior to placement in a hive.

12. A method of treating a beehive comprising:
providing a treatment device according to claim 1,
hanging the treatment device within a beehive to present the outer surfaces of the device for bees to walk over and disperse miticide throughout the hive.

13. A method of making a treatment device for treating a beehive comprising:
providing a strip comprising at least one layer, the or each layer formed from a biodegradable material permeable to water which is capable of being removed by bees,
providing a longitudinal reinforcement or join to or adjacent each longitudinal edge of the strip, to provide a longitudinal barrier to mechanically resist bees in the hive attacking and removing the or each layer of the device, wherein each reinforcement or join is a line of stitching, and
soaking the strip in a miticide to saturate the strip.

14. The method as claimed in claim 13, wherein the strip comprises a plurality of layers and the method comprises providing the plurality of layers and joining the layers together to allow for transfer of the miticide between layers as the miticide is removed from an outer surface of the strip during use.

15. The method of claim 13, further comprising:
providing the at least one layer in a roll, unrolling the at least one layer from the roll or rolls as a continuous strip, and providing the reinforcement or join to or adjacent each longitudinal edge of the continuous strip in a continuous process,
cutting the continuous strip into individual strips, each individual strip to be placed in the beehive.

16. The method of claim 14, further comprising:
providing each layer in a roll, unrolling each layer and aligning and stacking the layers together to form a continuous strip, and providing the reinforcement or join to or adjacent each longitudinal edge of the continuous strip in a continuous process, and cutting the continuous strip into individual strips, each individual strip to be placed in the beehive.

17. The method as claimed claim 14, further comprising rolling the continuous strip into a roll, unrolling the continuous strip from the roll and cutting into the individual strips.

18. The method as claimed in claim 13, wherein the strip or roll of continuous strip is stored dry and is soaked in the miticide immediately prior to use.

* * * * *